(12) United States Patent
Atlee, III

(10) Patent No.: US 6,878,118 B2
(45) Date of Patent: Apr. 12, 2005

(54) ESOPHAGEAL STETHOSCOPE WITH SEPARATE COVER MEMBER

(76) Inventor: John L. Atlee, III, N71 W29436 Tamron La., Hartland, WI (US) 53029

( * ) Notice: Subject to any disclaimer, the term of this patent is extended or adjusted under 35 U.S.C. 154(b) by 0 days.

(21) Appl. No.: 10/360,227

(22) Filed: Feb. 6, 2003

(65) Prior Publication Data

US 2003/0120166 A1 Jun. 26, 2003

Related U.S. Application Data

(62) Division of application No. 09/488,793, filed on Jan. 21, 2000, now Pat. No. 6,626,841.

(51) Int. Cl.[7] .............................................. A61B 5/042
(52) U.S. Cl. ........................ 600/528; 600/380; 607/124
(58) Field of Search ................................ 600/374, 380, 600/528, 586; 607/124

(56) References Cited

U.S. PATENT DOCUMENTS

| | | | |
|---|---|---|---|
| 4,475,555 A | | 10/1984 | Linder |
| 5,370,679 A | | 12/1994 | Atlee, III |
| 5,394,880 A | | 3/1995 | Atlee, III |
| 5,431,696 A | | 7/1995 | Atlee, III |
| 5,715,816 A | * | 2/1998 | Mainiero et al. ........... 600/323 |
| 6,259,938 B1 | * | 7/2001 | Zarychta et al. ........... 600/380 |
| 6,266,549 B1 | * | 7/2001 | Melnikoff et al. .......... 600/380 |

FOREIGN PATENT DOCUMENTS

| | | |
|---|---|---|
| WO | WO 96/29927 | 10/1996 |
| WO | WO 99/59463 | 11/1999 |

* cited by examiner

Primary Examiner—George R. Evanisko
(74) Attorney, Agent, or Firm—Boyle, Fredrickson, Newholm, Stein & Gratz, S.C.

(57) ABSTRACT

An esophageal stethoscope includes a tubular flexible body having an acoustic input region. A carrier member, which is separate from the tubular flexible body, is selectively engageable with the tubular flexible body either proximally or distally of the acoustic input region. The carrier member carries one or more devices for providing esophageal recording, monitoring or stimulation functions. For transesophageal cardiac pacing, electrodes are mounted to the carrier member such that engagement of the carrier member with the tubular flexible body functions to convert the esophageal stethoscope to a pacing stethoscope. To carry out a sensing, recording or monitoring function, such as esophageal oximetry, one or more oximetry probes are mounted to the carrier member such that engagement of the carrier member with the esophageal stethoscope converts the stethoscope for use in an oximetry sensing application. A "universal" stethoscope includes engagement structures at predetermined locations along the length of the tubular flexible body, for use in engaging a stimulation carrier and/or a recording/monitoring carrier with the esophageal stethoscope.

8 Claims, 7 Drawing Sheets

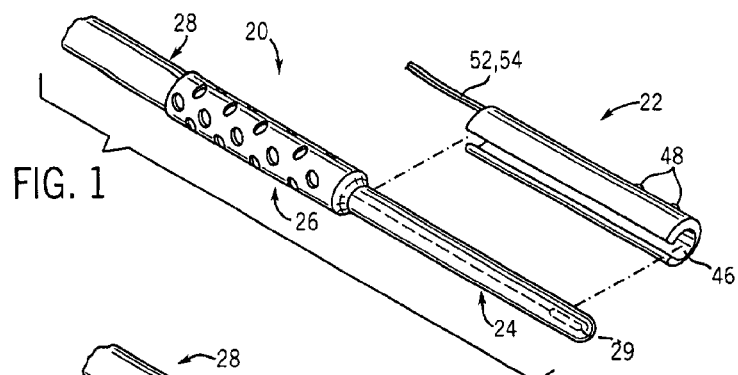
FIG. 1
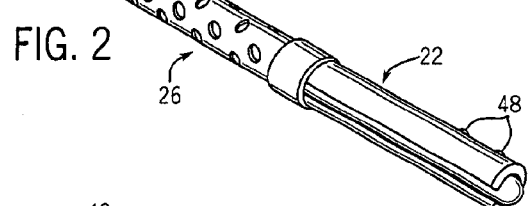
FIG. 2
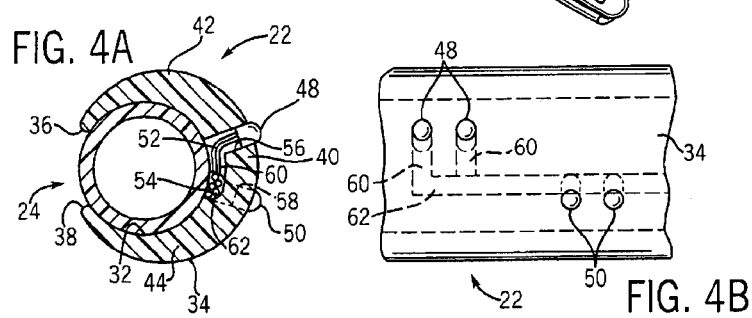
FIG. 4A
FIG. 4B
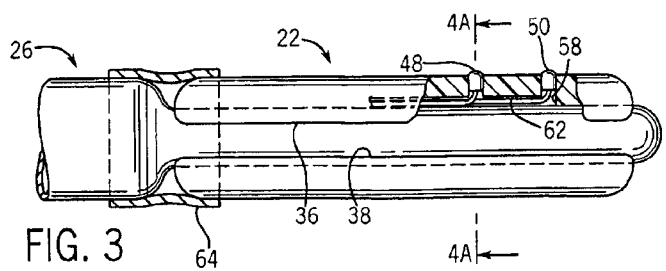
FIG. 3

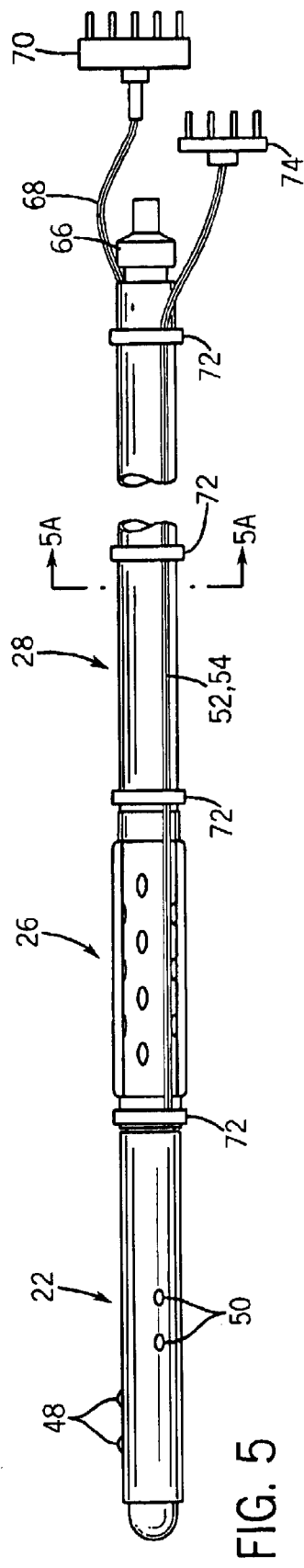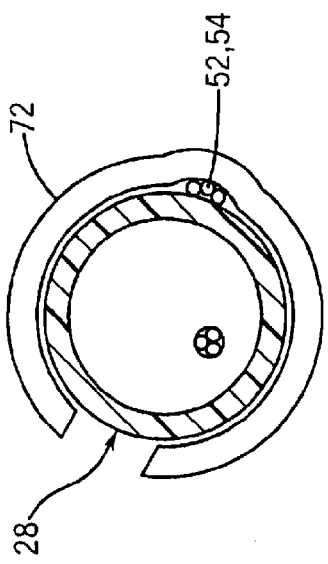
FIG. 5
FIG. 5A

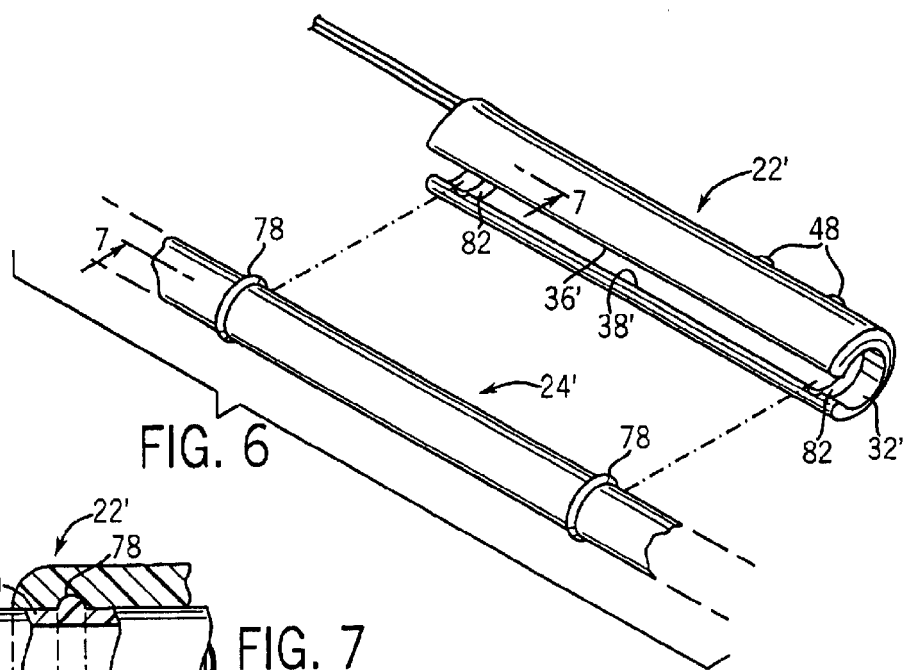
FIG. 6
FIG. 7
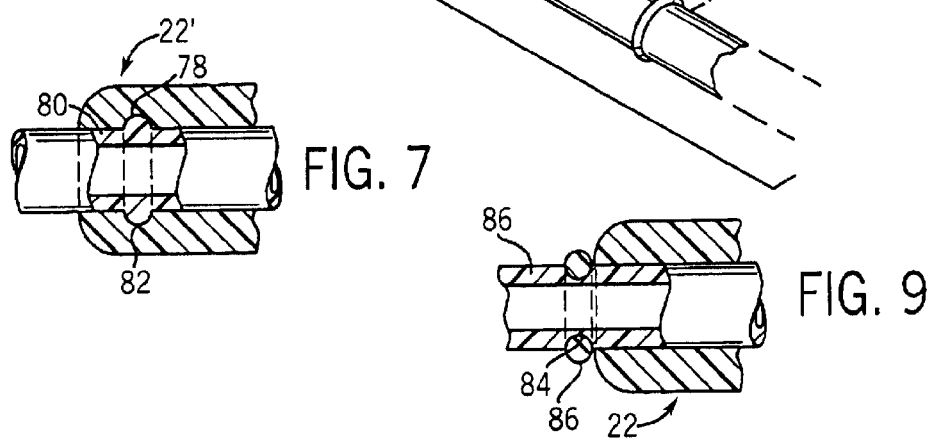
FIG. 9
FIG. 8
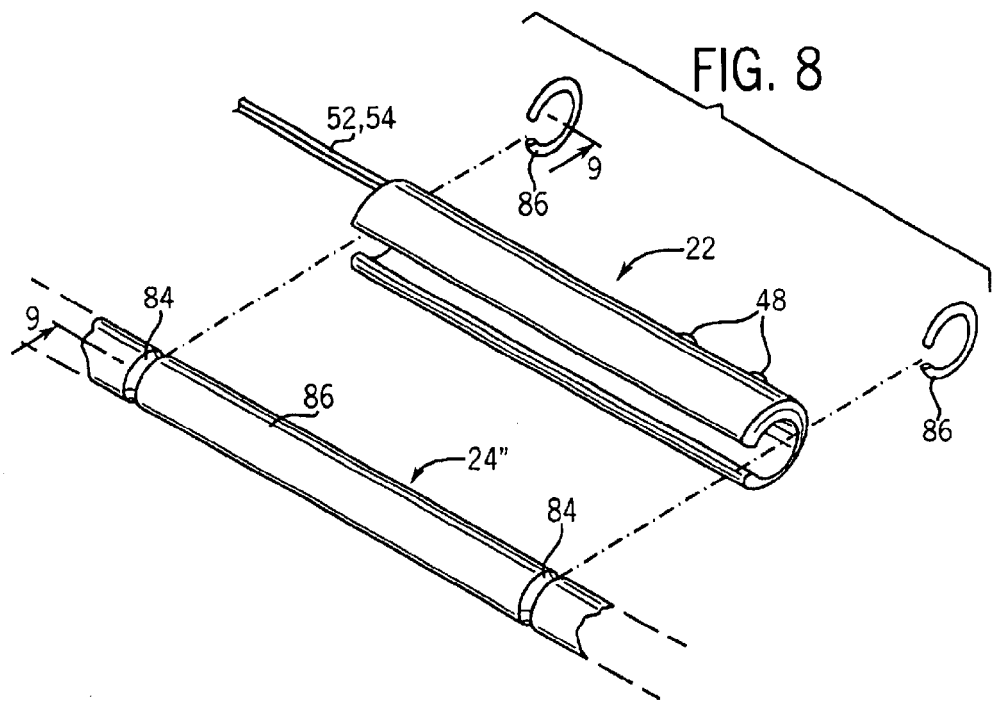

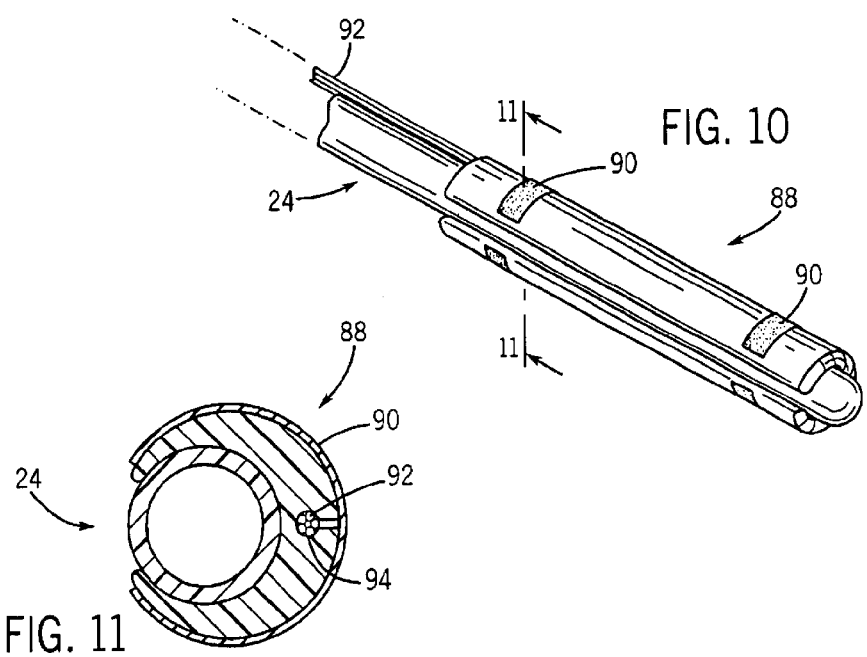
FIG. 10
FIG. 11
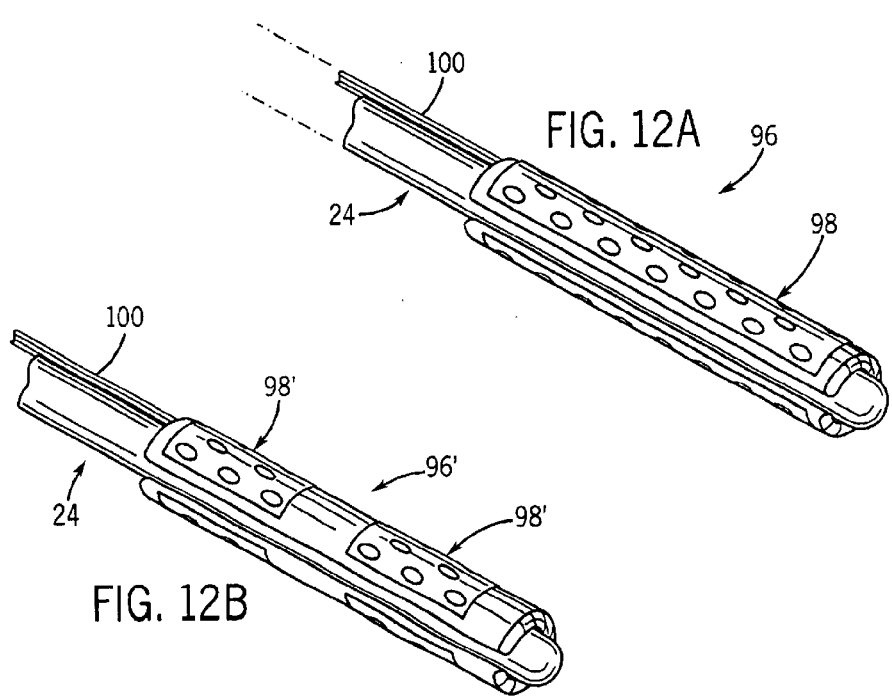
FIG. 12A
FIG. 12B

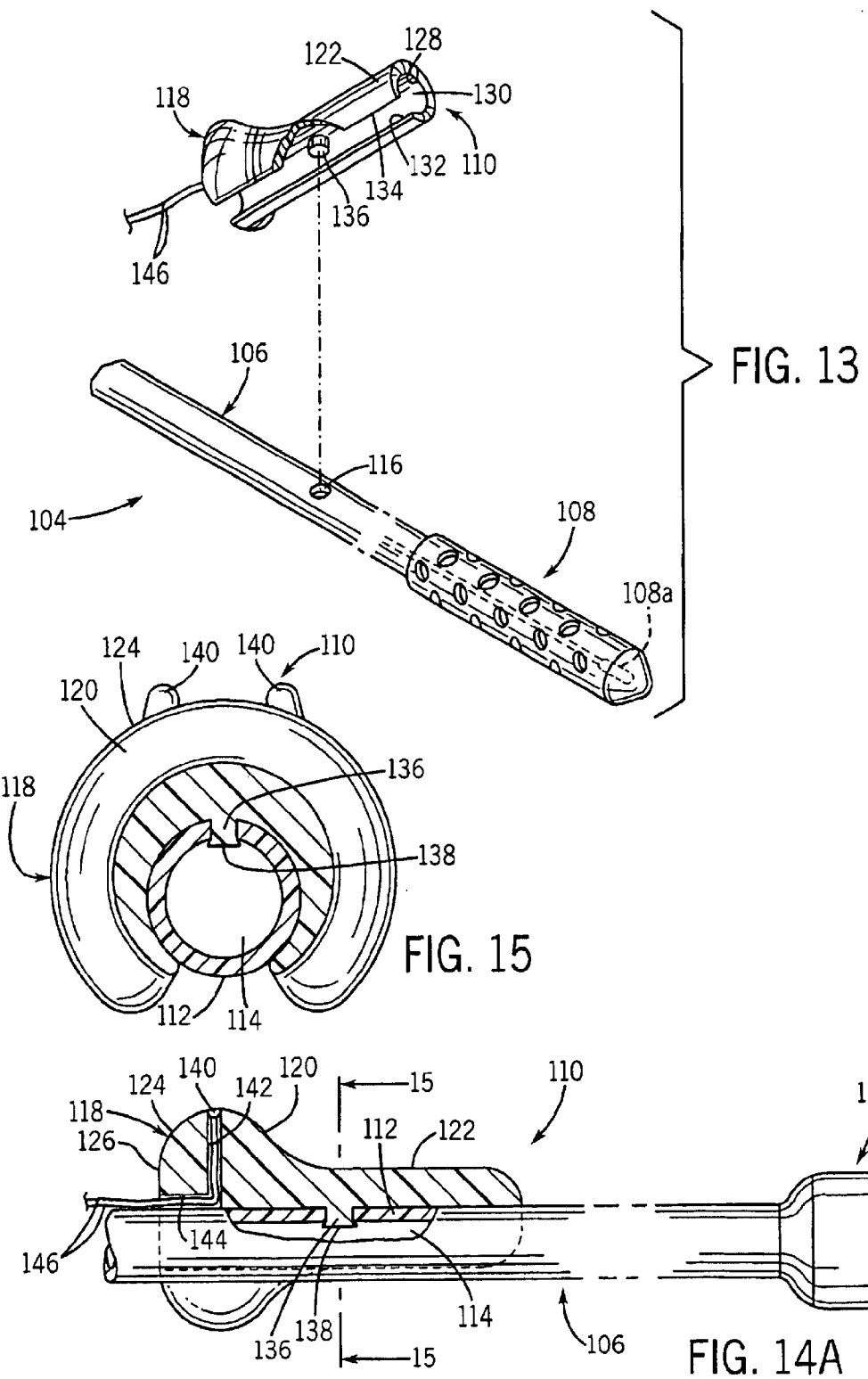

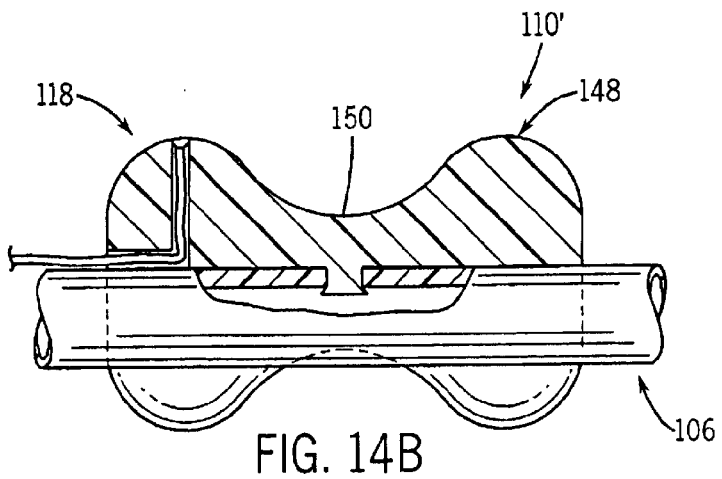
FIG. 14B
FIG. 16
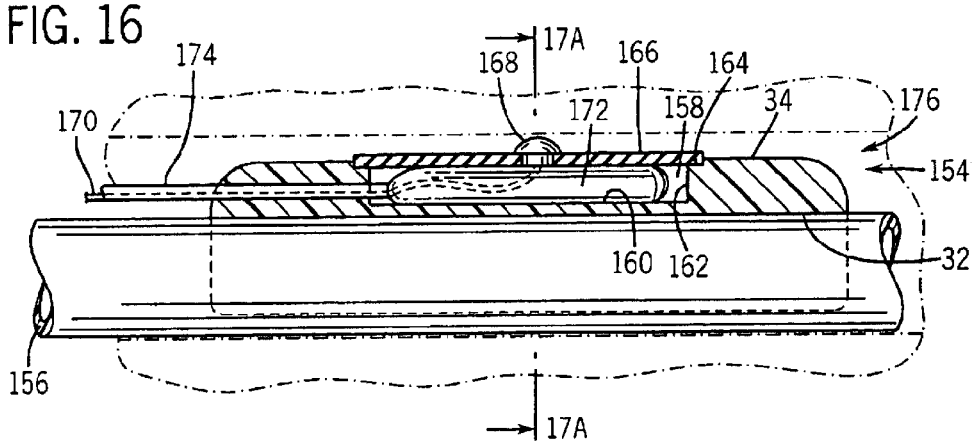
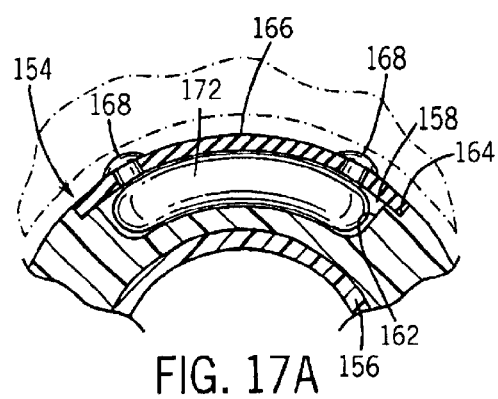
FIG. 17A
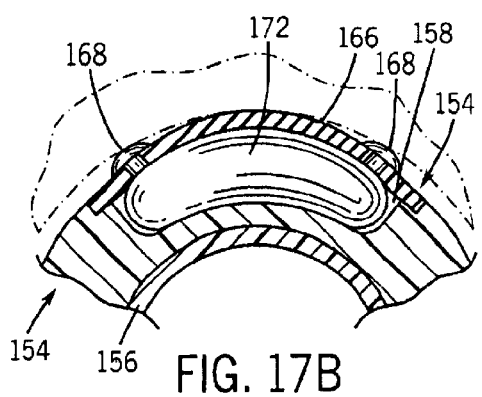
FIG. 17B

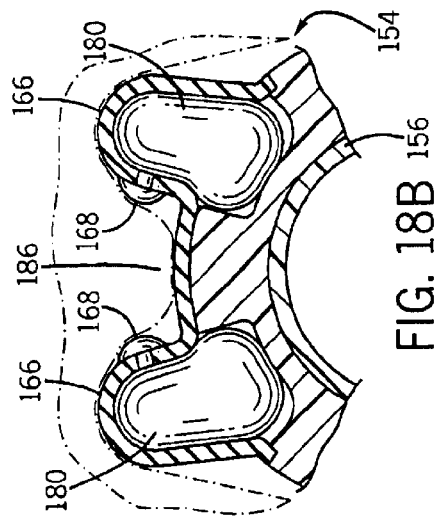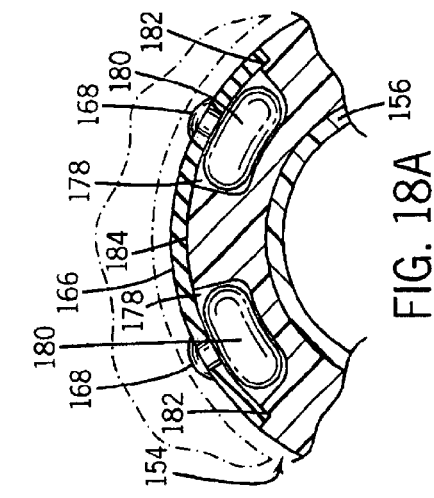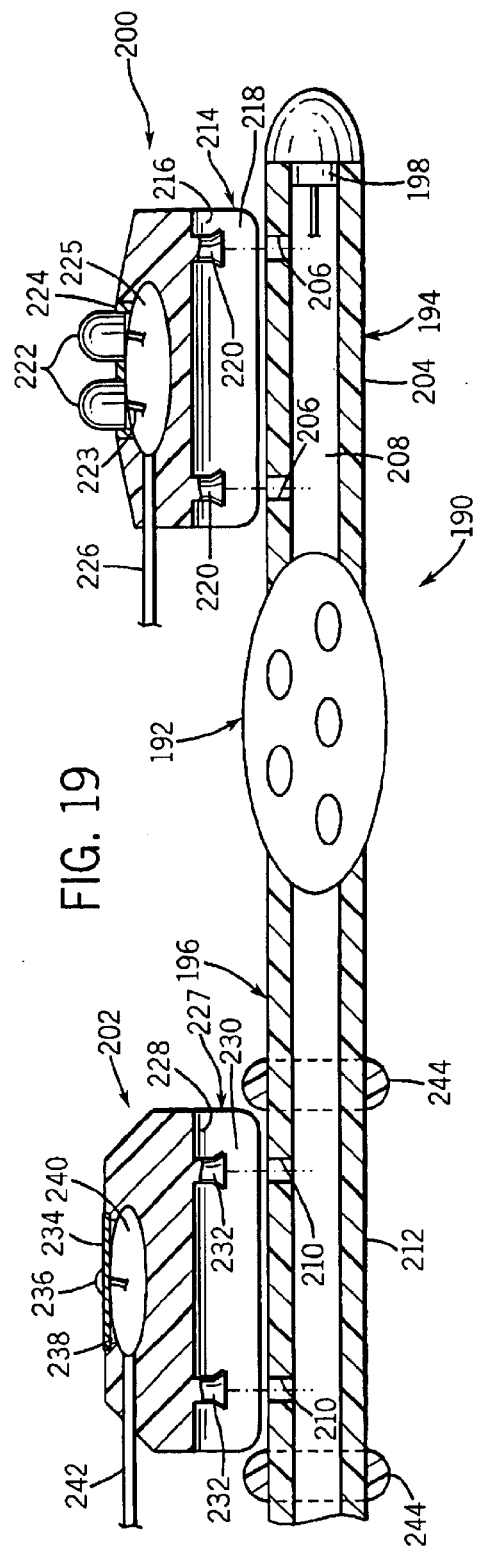

ESOPHAGEAL STETHOSCOPE WITH SEPARATE COVER MEMBER

CROSS-REFERENCE TO RELATED APPLICATION

This application is a divisional of application Ser. No. 09/488,793 filed Jan. 21, 2000 now U.S. Pat. No. 6,626,841.

BACKGROUND AND SUMMARY OF THE INVENTION

This invention relates to esophageal probes, and more particularly to an esophageal probe for performing recording, monitoring or stimulation functions from or within the esophagus, such as transesophageal monitoring of cardiac activity, transesophageal cardiac stimulation, such as cardiac pacing, or esophageal oximetry.

Esophageal probes are known in the art for performing various functions, such as cardiac monitoring, recording, pacing or electroversion. An esophageal probe may be in the form of an esophageal stethoscope which includes a diaphragm for listening to heart and breath sounds, and may incorporate a thermistor sensor for monitoring body temperature. An esophageal stethoscope may also be used for esophageal oximetry, in which oximetry measurements are obtained via oximetry probes in proximity to mucosal tissues within the esophagus.

Prior art esophageal probes used for transesophageal atrial pacing (TAP) applications typically incorporate either ring electrodes or point contact-type electrodes. In either version, the electrodes are fixed to the tubular wall of the probe, and wire leads extend through the internal passage of the probe and terminate in an external connector for coupling to a pacing apparatus. An example of a ring-type pacing probe is available from Cardio Command, Inc. of Tampa, Fla. under the designation TAPSCOPE.

Prior art esophageal oximetry probes typically include oximetry sensors mounted to a contoured structure secured to the tubular wall of the probe. The contoured structure is adapted for placement in a predetermined region within the esophagus of a patient, such that the oximetry probes are in close proximity to, or in contact with, the muscosal tissues of the esophagus in order to provide an accurate oximetry reading. Various satisfactory contoured structures are known, and examples are shown in U.S. Pat. Nos. 5,715,816 and 5,743,261, the disclosures of which are hereby incorporated by reference. Again, the oximetry sensors are interconnected with wire leads which are located within the internal passage of the probe and which terminate in a connector for coupling to an oximetry apparatus.

The above-described prior art esophageal probes have been found to provide satisfactory functions in listening to heart and breath sounds of a patient as well as for carrying out TAP and oximetry functions. Manufacture of TAP probes is complicated by mounting of the electrodes to the wall of the probe and placing the wire leads of the electrodes within the passage of the probe. The same holds true for oximetry probes, which require mounting of a contoured structure to the tubular probe and placement of the wire leads from the oximetry sensors within the passage of the probe. Accordingly, such probes are expensive and difficult to manufacture, and have met with limited acceptance by practitioners.

It is an object of the present invention to provide an esophageal probe, which preferably includes an acoustic pick-up and a thermistor element, and which provides capabilities for oximetry and/or cardiac pacing or other recording, monitoring or stimulation functions from or within the esophagus. It is a further object of the invention to provide such an esophageal probe which provides the basic capability of listening to heart and breath sounds and which also can be used for cardiac pacing, oximetry or other esophageal recording, monitoring and/or stimulation functions. Yet another object of the invention is to provide such an esophageal probe which is simple in its construction and which provides a high degree of flexibility in performing esophageal recording, monitoring and stimulation functions. A still further object of the invention is to provide such an esophageal probe which is relatively low in cost and simple in its components, assembly and operation. Yet another object of the invention is to provide such an esophageal probe which can be easily and quickly fitted with components for use in carrying esophageal recording, monitoring or stimulation functions.

In accordance with the invention, an esophageal probe generally includes a tubular flexible body having a proximal end and a distal end which is adapted to be placed into the esophagus of a patient. The probe may be in the form of an esophageal stethoscope, wherein the tubular flexible body includes an acoustic input region located toward the distal end for communicating heart and breath sounds through the tubular flexible body to the proximal end. The invention contemplates a carrier member, separate from the tubular flexible body, which is engageable with the tubular flexible body toward the distal end. The carrier member includes one or more accessories, devices or components for recording, monitoring and/or stimulating a condition within or from the esophagus of a patient. The carrier member defines a passage within which a portion of the tubular flexible body is received, for engaging the carrier member with the tubular flexible body. The carrier member may be in the form of a channel-type member having wall structure defining the passage and terminating in a pair of spaced apart ends. The space between the ends of the wall structure is in communication with the passage, and the tubular flexible body is adapted to pass through the space and into the passage. The wall structure may be formed of a resilient material, such that the spaced apart ends of the wall structure can be moved away from each other to allow the tubular flexible body to pass into the passage, and to thereafter allow the wall structure to move back together so as to engage the tubular flexible body.

Retainer structure is preferably interposed between the carrier member and the tubular flexible body for maintaining the carrier member in a desired axial position on the tubular flexible body. The retainer structure may be in the form of an opening formed in a wall of the tubular flexible body, and an engagement member associated with the carrier member and receivable within the opening in the wall of the tubular flexible body. In another form, the tubular flexible body is provided with one or more outward protrusion areas engageable with the carrier member. The outward protrusion areas may be in the form of one or more ring members, which may be engageable with the ends of the carrier member or received within a groove formed in an internal wall of the carrier member which defines the passage, for maintaining the carrier member in a predetermined axial position on the tubular flexible body. The ring member may be formed integrally with the wall of the tubular flexible body, or may be separate from and engageable with the wall of the tubular flexible body.

In one form, the carrier member carries a series of electrodes for use in transesophageal cardiac pacing and electrocardiography (ECG). The carrier member is preferably engaged with the tubular flexible body at a distal location relative to the acoustic input region, so as to preserve acoustic function while at the same time providing optimal positioning of the electrodes for use in cardiac pacing. The electrodes extend outwardly from an external surface defined by the carrier member, and each electrode is interconnected with one or more wire leads disposed within grooves or passages defined by the carrier member. The wire leads extend from a proximal end of the carrier member, and are located exteriorly of the tubular flexible body. The leads are preferably secured to the tubular flexible body, and terminate in a connector for coupling to a transesophageal or esophageal monitor and stimulator. In this manner, a basic esophageal stethoscope can be fitted for a cardiac pacing, ECG or other stimulation application such as DC cardioversion/defibrillation.

In another form, the carrier member carries an oximetric device such as one or more optodes (photoemitters, photodetectors) or the like. In this form, the carrier member is engaged with the tubular flexible body at a proximal location relative to the acoustic pick-up region, so as to place the optodes at an optimal location within the esophagus for obtaining oximetry readings. The carrier member may be in the form of a contoured member corresponding to the configuration of mucosal tissues within the esophagus, for placing the optodes in close proximity to the mucosal tissues. The optodes may be mounted to a deformable area associated with the carrier member located over a recess, with an inflatable member being located within the recess. In this manner, inflation of the inflatable member functions to outwardly deform the deformable area so as to contact the optodes with the mucosal tissues of the esophagus, to obtain accurate oximetry inputs. Alternatively, each of a pair of optodes may be mounted to a separate deformable area located over one of a pair of recesses. An inflatable member is located within each recess, and inflation of the inflatable members deforms the deformable areas such that the optodes face each other with mucosal tissues therebetween, to provide highly accurate oximetry readings. The optodes may be designed to carry out either transmissive oximetry or reflectance oximetry.

With this construction, an esophageal stethoscope can be provided with either stimulation or pacing capabilities or oximetry or other monitoring or recording capabilities, or both, simply by engaging either a stimulation carrier or a monitoring/recording carrier, or both, with the tubular flexible body of the esophageal stethoscope. This allows a user to customize the capabilities of an esophageal probe according to the needs of a particular patient. This also provides a manufacturer with significant flexibility in manufacture and production, by utilizing a basic stethoscope structure with add-on capabilities. A stethoscope can thus be used for a wide variety of applications with on-site adaptations according to patient requirements and other criteria. This reduces the overall cost and complexity of esophageal stethoscope assemblies, thus lowering production costs, while providing a wide variety of capabilities for the stethoscope and a wide variety of end use applications.

The invention further contemplates a method of adapting an esophageal stethoscope for use in carrying out various recording, monitoring and/or stimulation functions, as well as an esophageal stethoscope for receiving one or more carrier members adapted to provide esophageal recording, monitoring, or stimulation functions, substantially as summarized above.

Various other features, objects and advantages of the invention will be made apparent from the following description taken together with the drawings.

BRIEF DESCRIPTION OF THE DRAWINGS

The drawings illustrate the best mode presently contemplated of carrying out the invention.

In the drawings:

FIG. 1 is a partial isometric view of an esophageal stethoscope and a separate carrier member for mounting an accessory or device, such as electrodes for use in transesophageal cardiac stimulation, to the esophageal stethoscope;

FIG. 2 is a view similar to FIG. 1, showing the carrier member engaged with the esophageal stethoscope;

FIG. 3 is a partial side elevation view of the esophageal stethoscope and carrier member of FIG. 2;

FIG. 4A is a section view taken along line 4A—4A of FIG. 3;

FIG. 4B is a partial side elevation view showing the transesophageal cardiac pacing electrodes mounted to the carrier member of FIGS. 1–3;

FIG. 5 is a full side elevation view of the esophageal stethoscope with the carrier member mounted thereto as illustrated in FIGS. 2 and 3;

FIG. 6 is a view similar to FIG. 1, showing a portion of the esophageal stethoscope and a carrier member, and retainer structure for maintaining the carrier member in a predetermined axial position relative to the esophageal stethoscope;

FIG. 7 is a partial section view taken along line 7—7 of FIG. 6;

FIG. 8 is a view similar to FIG. 6, showing an alternative retainer structure;

FIG. 9 is a partial section view taken along line 9—9 of FIG. 8;

FIG. 10 is a view similar to FIG. 2, showing an alternative embodiment for a carrier member adapted to mount transesophageal cardiac pacing electrodes to an esophageal stethoscope;

FIG. 11 is a section view taken along line 11—11 of FIG. 10;

FIGS. 12A and 12B are views similar to FIG. 10, showing alternative electrode arrangements for use in transesophageal cardiac stimulation;

FIG. 13 is a partial isometric view of an esophageal stethoscope and a separate carrier member for mounting an accessory or device, such as one or more oximetry sensors, to the esophageal stethoscope;

FIG. 14A is a partial side elevation view, with portions broken away, showing a portion of the esophageal stethoscope of FIG. 13 with the oximetry sensor carrier member mounted thereto;

FIG. 14B is a view similar to FIG. 14A, showing an alternative shape for the oximetry sensor carrier member;

FIG. 15 is a section view taken along line 15—15 of FIG. 14A;

FIG. 16 is a partial side elevation view somewhat similar to FIGS. 3 and 14A, showing an alternative carrier member construction for mounting accessories or devices, such as oximetry probes, to an esophageal stethoscope;

FIG. 17A is a section view taken along line 17A—17A of FIG. 16, showing the sensors mounted to a deformable membrane and an inflatable member in a deflated condition;

FIG. 17B is a view similar to FIG. 17A, showing inflation of the inflatable member for moving the oximetry sensors into contact with mucosal tissue within the esophagus of a patient;

FIG. 18A is a view similar to FIG. 17A, showing an alternative construction for mounting sensors to the carrier member and showing the inflatable members in a deflated condition;

FIG. 18B is a view similar to FIG. 18A, showing the inflatable members in an inflated condition for moving the sensors into contact with the mucosal tissue; and FIG. 19 is a side elevation view, partially in section, showing a stethoscope and a pair of carrier members adapted for mounting to the stethoscope for providing different functions of transesophageal recording, monitoring or stimulation.

DETAILED DESCRIPTION OF THE INVENTION

FIG. 1 illustrates the distal end area of an esophageal stethoscope 20 in combination with a carrier member 22 constructed in accordance with the invention. The general construction and details of esophageal stethoscope 20 are known in the art. Generally, esophageal stethoscope 20 is in the form of a tubular flexible body defining a distal end section 24 extending outwardly from an acoustic input region 26, with a main body section 28 extending inwardly from acoustic region 26. In a manner as is known, end section 24, acoustic region 26 and main body section 28 define an internal passage extending throughout the length of esophageal stethoscope 20. The end tip of distal end section 24 may be provided with a thermistor 29 with a wire lead located within the passage of esophageal stethoscope 20 for sensing temperature within the esophagus. Esophageal stethoscope may include a separate lumen for orogastric suctioning, in a manner as is known. Representatively, esophageal stethoscope 20 may be a stethoscope such as is available from Mallinckrodt Medical, Inc. of St. Louis, Mo. under its designation MON-A-THERM, Part No. 91047, although it is understood that other similar constructions are available and known.

As shown in FIGS. 1–4B, carrier member 22 is in the form of an elongated channel-shaped member including an arcuate inner wall 32 and an arcuate outer wall 34 which terminate in spaced apart ends 36, 38. Carrier member 22 has a cross-section in the shape of a crescent, defining a central area 40 of maximum thickness, and wing areas 42, 44 extending oppositely from central area 40 and gradually tapering in thickness toward ends 36, 38, respectively. Carrier member 22 is preferably formed of a resilient material, such that wing areas 42, 44 can be deflected away from each other to spread ends 36, 38 apart, with the resiliency of the material of carrier member 22 being operable to bias wing areas 42, 44 toward a closed position as shown in FIG. 4A against outward movement. Carrier member 22 may be formed of a material such as a medical grade polyvinyl chloride or silicone material, although it is understood that other satisfactory biocompatible materials may be employed.

Carrier member 22 has a length slightly less than the length of distal end section 24 of esophageal stethoscope 20. Carrier member 22 defines a proximal end and a distal end, and inner wall 32 functions to define an internal passage 46 which extends between the ends of carrier member 22 throughout its length. The space between spaced ends 36, 38 defines an entrance to internal passage 46.

A first pair of electrodes 48 and a second pair of electrodes 50 are mounted to carrier member 22. Electrodes 48 and 50 are radially spaced apart from each other approximately 30° to 450°, and are equally radially offset from the radial center of carrier member 22.

Wire leads 52 and 54 are interconnected with and extend from bipolar electrodes 48, 50, respectively. Each electrode of bipolar electrodes 48 is mounted within the end of a radial passage 56 formed in carrier member 22, and each electrode of bipolar electrodes 50 is mounted in the end of a radial passage 58 formed in carrier member 22. A transverse groove 60 extends laterally from the inner end of each radial passage 56, extending between each radial passage 56 and an axial trough 62 which extends from the location of the most distal electrode 48 to the proximal end of carrier member 22. Wire leads 52 from bipolar electrodes 48 are routed through radial passages 56 and transverse grooves 60 to trough 62. Wire leads 54 from bipolar electrodes 50 are routed through radial passages 58 to trough 62. In this manner, wire leads 52 and 54 come together at the intersection of radial passages 58 and trough 62, and extend proximally from electrodes 50 throughout the length of carrier member 22 between electrodes 50 and the proximal end of carrier member 22. Wire leads 52, 54 emerge from trough 62 at the proximal end of carrier member 22.

In an alternative arrangement, bipolar electrodes 48, 50 and wire leads 52, 54 may be insert molded in an injection molding process along with carrier 22 in a manner as is known. With this construction, wire leads 52, 54 are encapsulated within the material of carrier member 22, and electrodes 48, 50 are molded into the material of carrier member 22 so as to protrude outwardly from the outer surface of carrier member 22.

In order to adapt esophageal stethoscope 20 for use in transesophageal cardiac pacing or other stimulation, carrier member 22 is mounted to distal end section 24 of esophageal stethoscope 20 prior to insertion of esophageal stethoscope 20 into the esophagus of a patient. To accomplish this, the user spreads wing areas 42, 44 of carrier member 22 apart from each other, and distal end section 24 of esophageal stethoscope 20 is inserted through the space between ends 36, 38, and is received within internal passage 46 of carrier member 22 as shown in FIGS. 2, 3 and 4a. Once distal end section 24 is so positioned within internal passage 46, the user releases wing areas 42, 44, which return to the closed position of FIG. 4A in response to the resiliency of the material of carrier member 22, so as to firmly clamp carrier member 22 onto distal end section 24. This results in the assembly as shown in FIGS. 2, 3 and 4a, which converts esophageal stethoscope 20 from a conventional stethoscope providing temperature sensing and input of heart and breath sounds, to a pacing-type stethoscope so as to enable a practitioner to not only obtain temperature sensing and heart and breath sounds from the esophagus, but also to accomplish transesophageal ECG cardiac pacing or other stimulation using bipolar electrodes 48, 50 in a manner as is known. Once carrier member 22 is engaged with esophageal stethoscope 20 in this manner, the assembled components are inserted into the esophagus of a patient and employed in a conventional manner so as to carry out transesophageal ECG cardiac pacing as well as to sense temperature and listen to heart and breath sounds from the esophagus.

When carrier member 22 is mounted to distal end section 24 as shown and described, the proximal end of carrier member 22 is located adjacent the distal end of acoustic input region 26 the distal end of carrier member 22 is located slightly inwardly from the end of distal end section 24 of esophageal stethoscope 20. A resilient sleeve 64 may be fitted over the adjacent ends of carrier member 22 and acoustic region 26 so as to span the space therebetween. Sleeve 64 also functions to maintain carrier member 22 in axial position relative to distal end section 24.

When carrier member 22 is mounted to esophageal stethoscope 20 in this manner, wire leads 52, 54 from bipolar electrodes 48, 50, respectively, are located externally of esophageal stethoscope 20. FIG. 5 illustrates esophageal stethoscope 20 in its entirety which is of generally conventional construction. A standard luer acoustic adapter 66 is mounted to the proximal end of main body section 28. Conductors 68 from the thermistor located within distal end section 24 emerge from the end of main body section 28 adjacent acoustic adapter 66, and are interconnected with a connector 70 for coupling to a temperature display. With carrier member 22 mounted to distal end section 24, wire leads 52, 54 extend throughout the length of esophageal stethoscope 20 proximally of carrier member 22. Wire leads 52, 54 extend across acoustic input region 26, and are retained in position relative to main body section 28 by means of clip members 72 which are engaged with main body section 28 at intermittent locations along the length of main body section 28, for retaining wire leads 52, 54 in position and preventing wire leads 52, 54 from movement during placement and operation of esophageal stethoscope 20. Alternatively, wire leads 52, 54 may be secured and placed using conventional biocompatible tape, either wrapped about main body section 28 and wire leads 52, 54 at intermittent locations, or extending longitudinally along the length of main body section 28 so as to entirely enclose wire leads 52, 54.

Wire leads 52, 54 are interconnected at their proximal ends with a connector 74 for coupling to a pacing, monitoring or other stimulation device, in a manner as is known.

FIG. 6 illustrates an alternative carrier member 22' having a similar construction as carrier member 22 for mounting bipolar electrodes such as 48, 50 to esophageal stethoscope 20. In this embodiment, the distal end section of esophageal stethoscope 20, shown at 24', includes a pair of rings 78 at spaced locations. As shown in FIG. 7, rings 78 are formed integrally with the wall of distal end section 24, shown at 80. The inner wall of carrier member 22', shown at 32', is provided with grooves 82, which are formed so as to extend transversely about inner wall 32' between the spaced ends of carrier member 22' shown at 36', 38'. Grooves 82 have the same axial spacing as rings 78, such that rings 78 are received within grooves 82 when carrier member 22' is engaged with distal end section 24', in the same manner as described previously with respect to engagement of carrier member 22 with distal end section 24. With this construction, rings 78 and grooves 82 function as retainer structure to maintain the axial position of carrier member 22' relative to esophageal stethoscope 20.

FIG. 8 illustrates carrier member 22 as shown and described with respect to FIGS. 1–4, and a retainer arrangement for maintaining carrier member 22 in a predetermined axial position on esophageal stethoscope 20. In the embodiment of FIGS. 8 and 9, the distal end section of esophageal stethoscope 20, shown at 24", is provided with a pair of axially spaced grooves 84 formed in the wall of distal end section 24", shown at 86. A resilient C-shaped clamping ring 86 is engaged within each groove 84, as shown in FIG. 9. Grooves 84 are spaced apart a distance such that an end of carrier member 22 is located closely adjacent each ring 86 when rings 86 are received within grooves 84. With this arrangement, rings 86 function to prevent axial movement of carrier member 22 on distal end section 24", to maintain carrier member 22 in a predetermined axial location on esophageal stethoscope 20.

While integral rings 78 are illustrated in FIGS. 6 and 7 as engaging grooves 82 in inner wall 32' of carrier member 22', it is understood that separable rings, such as 86, may be used in place of integral rings 78 for receipt within grooves 82. Similarly, while separable rings 86 are shown in FIGS. 8 and 9 as located adjacent the ends of carrier member 22, it is understood that integral rings such as 78 could also be used in a similar location to maintain carrier member 22 in position.

FIG. 10 illustrates a carrier member 88 having a generally similar construction as carrier member 22. Carrier member 88 has a pair of ring-type electrodes 90 engaged with the outer wall of carrier member 88, preferably received within shallow recesses formed in carrier member 88. Wire leads 92 are interconnected with ring electrodes 90, and are received within a passage 94 formed in carrier member 88. Alternatively, wire leads 92 and ring electrodes 90 may be insert molded in an injection molding process along with carrier member 88, in a conventional manner, such that wire leads 92 are encapsulated within the material of carrier member 88. In either version, wire leads 92 extend from the proximal end of carrier member 88, and are secured to esophageal stethoscope 20 in the same manner as shown and described previously with respect to wire leads 52, 54 in FIG. 5.

While FIG. 10 illustrates a pair of ring electrodes, it is understood that a single ring electrode or a plurality of ring electrodes of varying width and material (e.g. stainless steel or other conductive material) may be mounted to carrier member 88.

FIG. 12A illustrates a carrier member 96 having a patch-type electrode array 98 mounted to its outer surface. Wire leads 100 are interconnected with patch-type electrode array 98, and extend through carrier member 96 in a similar manner as shown and described with respect to ring electrodes 90 of FIGS. 10 and 11. FIG. 12B illustrates a carrier member 96' having a pair of patch-type foil electrodes 98' mounted to its outer surface. Wire leads 100 are connected to electrodes 98', and extend through carrier member 96' in a similar manner as shown and described with respect to ring electrodes 90 of FIGS. 10 and 11.

The ring electrodes of FIG. 10, the patch electrodes of FIG. 12A, and the foil electrodes of FIG. 12B may be mounted to a carrier member along with bipolar electrodes such as 48, 50 and used for cardioversion or defibrillation, in a manner as is known.

Carrier members 88 and 96 are mounted to distal end section 24 of esophageal stethoscope 20 in the same manner as shown and described with respect to carrier member 22. Alternatively, it is understood that distal end section 24 may be received within the passage defined by any of the carrier member embodiments using an axial slide-in motion, in which distal end section 24 is slid axially into the internal passage defined by the carrier member. Ring-type retainers such as shown in FIG. 8 may then be employed to maintain the carrier member in position relative to distal end section 24. Alternatively, the frictional engagement of the carrier member with distal end section 24 may be sufficient to prevent axial movement of the carrier member relative to esophageal stethoscope 20. If desired, texturing may be provided on the surface of distal end section 24 and/or the inner surface of the carrier member defining the passage, for increasing friction therebetween to aid in maintaining the carrier member in position.

FIG. 13 illustrates an alternative esophageal stethoscope 104 which includes a tubular flexible main body section 106, and an acoustic input region 108 and a thermistor 108a located at the distal end of esophageal stethoscope 104. A carrier member 110 is adapted for engagement with main body section 106 adjacent and proximal to acoustic input region 108.

As shown in FIGS. 13, 14a and 15, main body section 106 includes a wall 112 defining an internal passage 114. An opening 116 is formed in wall 112 at a location spaced proximally from the proximal end of acoustic region 108.

Carrier member 110 has a configuration throughout its distal area and a portion of its medial area similar to that of carrier member 22. At its proximal area, carrier member 110 is formed with a radially enlarged proximal end section 118 defining a flared distal outer surface 120 which extends outwardly from an outer wall 122 defined by the medial and distal areas of carrier member 110. Enlarged proximal end section 118 further defines a curved outer surface 124 which extends between flared distal outer surface 120 and a proximal end surface 126. Flared distal outer surface 120, curved outer surface 124 and proximal end surface 126 cooperate to define a bulbous shape for enlarged proximal end section 118.

In a manner similar to carrier member 22, carrier member 110 defines a crescent cross-section and includes an inner wall 128 defining an axial passage 130, which extends throughout the length of carrier member 112. Carrier member 130 further defines a pair of spaced apart ends 132, 134, and the space between ends 132, 134 defines an entrance to passage 130. A protuberance or tab member 136 extends from inner wall 128 into passage 130.

Carrier member 110 is preferably formed of a resilient, deformable material similar to that of carrier member 22. Carrier member 110 is engaged with main body section 106 of esophageal stethoscope 104 in the same manner as described above, i.e. by spreading ends 132, 134 apart so as to insert main body section 106 therethrough in a transverse direction into passage 130. Carrier member 110 is positioned relative to main body section 106 such that tab member 136 is aligned with opening 116. In this manner, when carrier member 110 is engaged with main body section 106, tab member 136 is received within and extends through opening 116, as shown in FIG. 15, to fix the axial position of carrier member 110 relative to esophageal stethoscope 104. Tab member 136 may be provided with a flared, rounded or ellipsoid outer end 138, which functions to positively retain tab member 136 within opening 116. After placement of main body section 106 within passage 130 as described, the user releases ends 132, 134, so as to allow carrier member 110 to return to its position as illustrated in FIG. 15, in which carrier member 110 is clamped onto main body section 106.

It is understood that one or more members such as 136 may also be used in carrier members 22 and 88 to maintain the carrier member in position, with such tab(s) being engageable within one or more perforated openings in the wall of the tube.

A pair of oximetry transceivers, such as photoemitter and photodector optodes 140, are mounted to carrier member 110. Optodes 140 are positioned on curved outer surface 124, so as to face outwardly and toward each other. Each optode 140 is mounted in the outer end of a radial passage 142 formed in carrier member 110. Each radial passage 142 communicates at its inner end with a trough 144, which extends between proximal end surface 126 and radial passages 142. Wire leads 146 are interconnected with optodes 140 and extend through passages 142 and trough 144. Wire leads 146 are adapted for securement to main body section 106 in the same manner as described previously with respect to wire leads 52, 54, and terminate in a connector for coupling to an oximetry apparatus.

Optodes 140 function as oximetry transceivers when esophageal stethoscope 104 is placed into the esophagus of a patient. In a manner as is known, enlarged proximal end section 118 of carrier member 110 is adapted to engage the upper esophageal constrictor/outlet (cricopharyngeus muscle) within the esophagus, to locate esophageal stethoscope 104 in an optimal position within the esophagus for providing heart and breath sounds to acoustic input region 108. Specifically, in a preferred embodiment, optodes 140 are located 13.0 cm from the midpoint of acoustic input region 108. When enlarged proximal end section 118 is engaged with the esophagus in this manner, optodes 140 are engaged with the mucosal esophageal tissues so as to provide highly accurate oximetry readings. With this arrangement, mounting of carrier member 110 to esophageal stethoscope 104 provides oximetry capability to esophageal stethoscope 104 if desired for a particular application.

Opening 116 in wall 112 is preferably formed by initially providing wall 112 with a circular perforation corresponding to the shape of opening 116, such that the material of wall 112 remains in place at opening 116 during production and shipment. With this arrangement, an end user can employ esophageal stethoscope 104 as a conventional temperature sensing acoustic esophageal probe. If it is desired to adapt esophageal stethoscope 104 to provide an oximetry sensing function, carrier member 110 is mounted to main body section 106 in the manner as described above. The material of wall 112 at opening 116, as defined by the circular perforation in wall 112, may be removed by the user prior to engagement of carrier member 110 with main body section 106. Alternatively, the material of wall 112 may be left in place, and tab member 136 then functions to dislodge the material of wall 112 at opening 116 upon engagement of carrier member 110 with main body section 106. The disc of material which is the removed portion of wall 112 is forced into passage 114, and remains within passage 114 during use. The removed disc of material is sufficiently small so as not to interfere with the function of esophageal stethoscope 104 during use.

FIG. 14B illustrates a carrier member 110' which is similar in operation to carrier member 110. In addition to enlarged proximal end section 118, carrier member 110' further includes a similarly shaped enlarged distal end section 148 which cooperates with proximal end section 118 to define a recessed area 115 therebetween. The shape of carrier member 110' is operable to provide a positive engagement with the cricopharyngeal region of the proximal esophagus of a patient in a known manner, so as to positively retain esophageal stethoscope 104 in a predetermined position within the esophagus. Again, oximetry optodes 140 may be mounted to either or both of areas 118 or 148, for providing inputs to an oximetry apparatus in a conventional manner.

In addition to the illustrated carrier member configurations of FIGS. 13–15, it is understood that other satisfactory configurations or shapes may be employed to locate stethoscope 104 within approximately the upper third of the esophagus, and in particular with respect to the upper constricted area of the esophagus.

FIGS. 16–17 illustrate a carrier member 154 for mounting to an esophageal stethoscope. Carrier member 154 may be mounted in any position on the tubular flexible body of the stethoscope, such as to a distal end section such as 24 or to a main body section such as 104. The esophageal stethoscope includes a wall 156 defining the tubular flexible body at the location where carrier member 154 is mounted. Carrier member 154 has the same general construction and cross-section as carrier member 122, and is mounted to wall 156 in the same manner as described with respect to mounting of carrier member 22. To facilitate clarity, the same reference characters as for carrier member 22 will be used where possible for carrier member 154.

Carrier member 154 includes a recess 158 extending inwardly from outer wall 34. Recess 158 is defined by a bottom wall 160 and a series of side walls 162. A shoulder 164 is formed at the upper extent of each side wall 162. A flexible, resilient membrane 166 overlies recess 158, and the edges of membrane 166 are received within and fixed to shoulders 164. A pair of sensing or stimulation devices 168 are mounted to membrane 166. Devices 168 may be in the form of pacing or ECG electrodes, oximetry optodes or any other device for providing esophageal recording, monitoring or stimulation, such as but not limited to Doppler (ultrasound) flow detectors or apparatus for measuring aortic dimension (e.g. m-mode echocardiography) for monitoring cardiac output. Devices 168 include wire leads 170.

An inflatable member 172 is received within recess 158, and is disposed between recess bottom wall 160 and the underside of membrane 166. A tube 174 extends proximally from inflatable member 172. Wire leads 170 and tube 174 may be received within a passage extending proximally from recess 158 so as to extend from the proximal end of carrier member 154. Alternatively, the material of carrier member 154 may be molded about tube 174 and wire leads 170. In a manner as is known, a syringe adapter is mounted to the proximal end of tube 174, such that a fluid, such as a liquid or air, can be introduced through tube 174 and into inflatable member 172.

Wire leads 170 and tube 174 extend along the esophageal stethoscope and are secured thereto in the same manner as shown and described previously with respect to wire leads 52, 54.

In use, once the esophageal stethoscope is inserted into the esophagus of a patient, as is shown schematically at 176 in FIGS. 16–18, fluid (or air) is introduced through tube 174 into inflatable member 172. In this manner, inflatable member 172 bears against bottom wall 160 of recess 158, and functions to deform membrane 166 outwardly relative to outer wall 34 of carrier member 154 as shown in FIG. 17B. This outward deformation of membrane 166 brings devices 168 into contact with the wall of esophagus 176. With this arrangement, devices 168 are able to provide an effective esophageal recording, monitoring or stimulation function due to the positive contact between devices 168 and the esophageal wall.

FIGS. 18A and 18B illustrate an alternative embodiment in which carrier member 154 is provided with a pair of recesses 178 and an inflatable member 180 is received within each recess 178. Membrane 166 is fixed at its edges to shoulders 182, and to the area between recesses 178, shown at 184. With this arrangement, inflation of inflatable members 180 functions to bias membrane 166 outwardly at spaced locations corresponding to the locations of recesses 178. Devices 168 are mounted to membrane 166 such that, upon inflation of inflatable members 180, devices 168 face each other with an area of esophageal mucosal tissue, shown at 186, located between devices 168. With devices 168 as oximetry sensors such as optodes, the oximetry reading obtained through mucosal tissue area 186 provides a highly accurate esophageal oximetry input.

It should be understood that sensing and/or stimulation devices, such as 168, may be mounted to a membrane in any desired location on a carrier member such as 154. It should also be understood and appreciated that the carrier member may have any shape, e.g. a shape as shown and described with respect to FIGS. 13–15, and is not limited to the specific configuration as illustrated.

FIG. 19 illustrates an esophageal stethoscope 190 having an acoustic input region 192 located between a distal end section 194 and a main body section 196. A thermistor 198 is preferably mounted at the end of distal end section 194, in a manner as is known. A lumen may be incorporated into stethoscope 190 for gastric suctioning, also in a manner as is known (e.g. such as is incorporated into a stethoscope available from Mallinckrodt under its designation MONATH-ERM XL with gastric suctioning).

FIG. 19 schematically illustrates a stimulation carrier member 200 adapted for engagement with distal end section 194, and a recording or monitoring carrier member 202 adapted for engagement with main body section 196. Esophageal stethoscope 190 is a "universal" stethoscope, providing the capability of mounting either stimulation carrier 200 or recording/monitoring carrier 202, or both, to enhance the operation of esophageal stethoscope 190 beyond simply providing esophageal temperature detection and listening to esophageal heart and lung sounds. The configuration of carrier members 200 and 202 is shown schematically, and it is understood that the actual configuration of carrier members 200, 202 may be as illustrated in FIGS. 1–18, or any other configuration may be employed as desired.

The wall of distal end section 194, shown at 204, is provided with a pair of spaced openings 206 which communicate between the internal passage of distal end section 194, shown at 208, and the exterior of distal end section 194. Similarly, a pair of openings 210 are formed in the wall of main body section 196, shown at 212. Openings 206 and 210 are at predetermined optimal locations relative to acoustic input region 196 and the end of distal end section 194. Preferably, openings 206, 210 are formed in the same manner as described above with respect to opening 116, i.e. by forming initial circular perforations in walls 204, 212.

Stimulation carrier 200 includes spaced wing areas 214 constructed similarly to wing areas 42, 44 of carrier member 22. The wing areas, such as 214, of stimulation carrier 200 terminate in spaced ends, and define an inner wall 216 forming a passage 218. Tab members 220, which includes rounded or ellipsoid end areas, extend inwardly from inner wall 216 into passage 218, and are spaced apart the same spacing as openings 206. With this construction, stimulation carrier 200 is engaged with distal end section 194 as described above, by inserting distal end section 194 through the space between wing areas 214 and into passage 218. Tab members 220 extend through openings 206, for maintaining stimulation carrier 200 in a predetermined axial position relative to esophageal catheter 190. Again, the push-on engagement of stimulation carrier 200 with distal end section 194 functions to press the material of wall 204 at openings 206 into passage 208, where the removed discs of material remain during use without interfering with the operation of esophageal stethoscope 190. Stimulation carrier 200 includes a series of stimulation accessories or devices, such as electrodes 222, which are spaced apart and angularly offset from each other to provide an optimal stimulation arrangement, such as for transesophageal cardiac pacing or ECG. Wire leads 223 extend from electrodes 222. Stimulation carrier 200 may include a deformable membrane 224 over a recess within which an inflatable member 225 is received for deflecting electrodes 222 outwardly toward the esophageal walls when in use, as described above. A sheath 226 extends from the proximal face of stimulation carrier 200, and wire leads 223 are received within sheath 226 along with the inflation tube for inflatable member 225. Sheath 226 is secured to distal end section 194 and main body section 196 as described previously.

Recording/monitoring carrier 202 has essentially the same structure as stimulation carrier 200, including wing areas 227, an inner wall 228 defining a passage 230, and tab members 232 extending into passage 230 from inner wall 228. Tab members 232 are adapted to be engaged with openings 210 upon placement of main body section 196 within passage 230 defined by recording/monitoring carrier 202, to maintain recording/monitoring carrier 202 in a predetermined axial position on esophageal stethoscope 190. As described previously with respect to FIGS. 16–18, recording/monitoring carrier 202 may include a membrane 234 to which one or more recording/monitoring accessories or devices 236, such as oximetry transceivers, are mounted. Membrane 234 is positioned over a recess 238, and an inflatable member 240 may be located within recess 238 for selective inflation through an inflation tube 242 for moving accessories or devices 236 into contact with, or in closer proximity to, the mucosal tissues of the esophagus for accurate monitoring or recording of esophageal conditions.

If desired, rings 244 may be mounted to or formed integrally with wall 212 of main body section 196. Rings 244 may be used in place of openings 210 and tab members 232 for retaining recording/monitoring carrier 202 in position on main body section 196 and defining the location for engagement of carrier 202, or may be used in combination with openings 210 and tab members 232. Similar structure may be provided for stimulation carrier 200 in place of or in combination with openings 206 and tab members 220. In addition, the location for engagement of carriers 200, 202 may be identified using one or more colored or otherwise differentiated lines or surfaces on body section 196, which provide a visual indication to the user as to proper placement of carriers 200, 202.

Esophageal stethoscope 190 is preferably manufactured with engagement structure such as openings 206, 210 or rings 244, located in predetermined positions relative to the tip of esophageal stethoscope 190 and/or acoustic input region 192. This engagement structure enables a user to mount either or both of stimulation carrier 200 and recording/monitoring carrier 202 to esophageal stethoscope 190, according to the desired functioning to be performed by esophageal stethoscope 190. The wire leads from carriers 200 and/or 202 are secured to esophageal stethoscope 190 in the same manner as described previously with respect to wire leads 52, 54.

The drawings illustrate the tabs such as 136, 220, 232 as being formed on the carriers such as 110, 200 and 202, respectively, and being receivable within openings formed in the main body section of the stethoscope. It should also be understood that a reverse configuration could be employed, in which tabs are formed in or mounted to the main body section of the stethoscope and are received within openings formed in the wall of the carrier which engages the stethoscope.

The universality of esophageal stethoscope 190 greatly facilitates esophageal recording, monitoring and/or stimulation by allowing a user to customize the esophageal stethoscope configuration according to requirements for a particular case. Universal esophageal stethoscope 190 involves minor modifications to existing esophageal stethoscope technology, with the primary modification being the provision of engagement structure both at a distal location and a proximal location relative to acoustic input region 192 and the distal tip of distal end section 194. Esophageal stethoscope 190 can thus be used alone without stimulation carrier 200 and recording/monitoring carrier 202, to sense and record temperature utilizing thermistor 198 and to listen to esophageal heart and breath sounds utilizing acoustic input region 192. Stimulation carrier 200 is engaged with esophageal stethoscope 190 when it is desired to provide a stimulating function within the esophagus, such as transesophageal cardiac pacing. Recording/monitoring carrier 202 is engaged with esophageal stethoscope 190 when it is desired to monitor or record a condition within the esophagus, such as oximetry. Carriers 200 and 202 can be used separately or in combination, according to the requirements of a particular case.

It is understood that carriers such as 200, 202 may be configured and arranged relative to stethoscope 190 to provide a range of functions such as cardiac pacing, echocardiography, oximetry, cardiac output monitoring, cardioversion, defibrillation, etc.

The accessories or devices shown in the drawings and described herein have been characterized as electrodes, optodes or the like. It should be understood that the invention can be utilized to mount any type of device or accessory to a stethoscope or other member adapted for placement into a body passage such as the esophagus, and is not limited to the illustrated and described accessories or devices. Examples of other types of devices or accessories include transducers, m-mode contacts, doppler pick-ups, temperature sensors, cardiac output or dimension sensors, etc. In addition to use in connection with an esophageal stethoscope, the device or accessory carrier system of the invention may also be adapted with any other tubes or probes that reside in the esophagus, such as an orogastric tube, nasogastric tube, transesophageal echocardiography probe, gastroscope, esophagoscope. Representative applications of the present invention include, but are not limited to, electrocardiography, cardiac pacing, DC cardio version or defibrillation, esophageal oximetry, cardiac output determinations, monitoring of respiratory gases, e.g. for oxygen, carbon dioxide, anesthetic or drug content, reflectance or transmissive spectrophotometry, detection of core body temperature, sensing of core tissue perfusion, and delivery of drugs and other substances for medicinal or diagnostic purposes.

The invention thus provides a simple, unique and effective way to provide an esophageal stethoscope with stimulation, sensing, recording or monitoring capabilities.

It should be appreciated and understood that the invention may be used in both human and veterinary applications.

Various alternatives and embodiments are contemplated as being within the scope of the following claims particularly pointing out and distinctly claiming the subject matter regarded as the invention.

I claim:
1. An esophageal stethoscope assembly, comprising:
a tubular flexible body having a proximal end and a distal end, and including an acoustic input region defined on the tubular flexible body toward the distal end;
a carrier member separate from the tubular flexible body and engageable with the tubular flexible body, wherein the carrier member includes one or more devices for sensing and/or controlling a condition from or within the esophagus of a patient, wherein the tubular flexible body extends along a longitudinal axis, and wherein the carrier member defines an axial passage and includes wall structure defining a pair of spaced ends, wherein the space between the spaced ends of the wall structure is in communication with the axial passage, and wherein the carrier member is engageable with the tubular flexible body by application of a push-on force transverse to the longitudinal axis of the tubular flexible body such that the tubular flexible body passes through the space between the wall structure ends and into the axial passage of the carrier member, wherein the carrier member wall structure is formed of a resilient material such that the wall structure is separable to enlarge the space between the wall structure ends to allow the tubular flexible body to pass therethrough into the axial passage of the carrier member, and wherein the resiliency of the wall structure is operable to thereafter engage the wall structure with the tubular flexible body; and a retainer structure interposed between the carrier member and the tubular flexible body for maintaining the carrier member in a predetermined axial position relative to the tubular flexible body.

2. The esophageal stethoscope assembly of claim 1, wherein the carrier member is engageable with the tubular flexible body distally of the acoustic input region and wherein the one or more devices comprise a series of pacing electrodes carried by the carrier member.

3. The esophageal stethoscope assembly of claim 1, wherein the carrier member is engageable with the tubular flexible body proximally of the acoustic input region and wherein the one or more devices comprise one or more oximetry sensors carried by the carrier member.

4. The esophageal stethoscope assembly of claim 1, wherein the carrier member is engageable with the tubular flexible body distally of the acoustic input region and wherein the one or more devices comprise a series of pacing electrodes, and further comprising a second carrier member separate from the tubular flexible body and engageable with the tubular flexible body proximally of the acoustic input region, wherein the proximal second carrier member carries one or more oximetry sensors.

5. An esophageal stethoscope assembly, comprising:

a tubular flexible body having a proximal end and a distal end, wherein the tubular flexible body defines a length and includes an acoustic input region located toward the distal end;

a carrier member separate from the tubular flexible body and engageable with the tubular flexible body, wherein the carrier member has a length less than that of the tubular flexible body and includes one or more devices for sensing and/or controlling a condition from or within the esophagus of a patient; and one or more electrical lead wires, wherein the one or more devices are interconnected with the one or more electrical lead wires, wherein the carrier member has a proximal end and defines passage structure for receiving the one or more electrical lead wires and wherein the passage structure is oriented such that the one or more electrical lead wires extend from a proximal end defined by the carrier member, and wherein the electrical lead wires are located exteriorly of the tubular flexible body and are exposed between the carrier member and the proximal end of the tubular flexible body.

6. The esophageal stethoscope assembly of claim 5, further comprising one or more retainers separate from the carrier member and engaged with the one or more electrical lead wires and with the tubular flexible body.

7. An esophageal stethoscope assembly, comprising:

a tubular flexible body having a proximal end and a distal end, wherein the tubular flexible body defines a length and inches an acoustic input region located toward the distal end;

a carrier member separate from the tubular flexible body and engageable with the tubular flexible body, wherein the carrier member has a length less than that of the tubular flexible body and includes one or more devices for sensing and/or controlling a condition from or within the esophagus of a patient; and one or more electrical lead wires, wherein the one or more devices are interconnected with one or more electrical lead wires and wherein the one or more electrical lead wires extend from the carrier member, and wherein the electrical lead wires are located exteriorly of the tubular flexible body when the carrier member is engaged with the flexible body and are exposed between tile carrier member and the proximal end of the tubular flexible body.

8. The esophageal stethoscope assembly of claim 7, further comprising one or more retainers separate from the carrier member and engaged with the one or more electrical lead wires and with the tubular flexible body.

* * * * *

UNITED STATES PATENT AND TRADEMARK OFFICE
CERTIFICATE OF CORRECTION

PATENT NO.    : 6,878,118 B2
DATED         : April 12, 2005
INVENTOR(S)   : Atlee, III It is certified that error appears in the above-identified patent and that said Letters Patent is hereby corrected as shown below:

Column 16,
Line 24, delete "inches" and substitute therefore -- includes --;
Line 38, delete "tile" and substitute therefore -- the --.

Signed and Sealed this

Sixteenth Day of August, 2005

JON W. DUDAS
*Director of the United States Patent and Trademark Office*